United States Patent [19]

Saito et al.

[11] Patent Number: 5,030,874
[45] Date of Patent: Jul. 9, 1991

[54] ULTRASONIC PROBE

[75] Inventors: Koetsu Saito, Nakano; Masami Kawabuchi, Yokohama, both of Japan

[73] Assignee: Matsushita Electric Industrial Co., Ltd., Osaka, Japan

[21] Appl. No.: 455,797

[22] Filed: Dec. 28, 1989

Related U.S. Application Data

[63] Continuation of Ser. No. 203,526, May 20, 1988, abandoned, which is a continuation of Ser. No. 865,011, May 20, 1986, abandoned.

[30] Foreign Application Priority Data

May 20, 1985 [JP] Japan ................................ 60-107355
May 20, 1985 [JP] Japan ................................ 60-107356
Jul. 23, 1985 [JP] Japan ................................ 60-162404

[51] Int. Cl.$^5$ ............................................ H01L 41/08
[52] U.S. Cl. ..................................... 310/334; 310/358; 310/800; 310/366
[58] Field of Search ........................ 310/334–336, 310/357–359, 800, 366, 363, 364

[56] References Cited

U.S. PATENT DOCUMENTS

| | | | |
|---|---|---|---|
| 4,217,684 | 8/1980 | Brisken et al. | 310/334 |
| 4,385,255 | 5/1983 | Yamaguchi et al. | 310/366 X |
| 4,409,510 | 10/1983 | Assenza et al. | 310/334 |
| 4,424,465 | 1/1984 | Ohigashi et al. | 310/336 X |
| 4,462,092 | 7/1984 | Kawabuchi et al. | 310/336 X |
| 4,467,237 | 8/1984 | Piaget et al. | 310/334 |
| 4,469,976 | 9/1984 | Scott | 310/334 |
| 4,482,834 | 11/1984 | Dias et al. | 310/334 X |
| 4,616,152 | 10/1986 | Saito et al. | 310/334 |
| 4,644,214 | 2/1987 | Takamizawa et al. | 310/335 X |
| 4,676,106 | 6/1987 | Nagai et al. | 310/334 |
| 4,686,408 | 8/1987 | Ishiyama | 310/335 X |
| 4,704,774 | 11/1987 | Fujii et al. | 310/335 X |
| 4,747,192 | 5/1988 | Rokurota | 310/334 X |

FOREIGN PATENT DOCUMENTS

| 0031298 | 2/1982 | Japan | 310/334 |
|---|---|---|---|
| 0072299 | 4/1984 | Japan | 310/334 |

*Primary Examiner*—Mark O. Budd
*Attorney, Agent, or Firm*—Wenderoth, Lind & Ponack

[57] ABSTRACT

Disclosed is an ultrasonic probe using a compound piezoelectric material made of piezoelectric ceramic and organic polymer. On one principal plane of the compound piezoelectric material, electrodes and electric terminals conducting to these electrodes are formed, and these electrodes and electric terminals are divided into a plurality. On the other principal plane of the compound piezoelectric material, a common electrode is provided, and an acoustic matching layer is mounted on it either intact or divided in correspondence to the divided electrodes. By using part of the compound piezoelectric material as the electric terminal take-out portion, the mechanical strength of the electric terminal take-out portion can be improved, which is particularly preferable for the ultrasonic probe driven at high frequency.

4 Claims, 4 Drawing Sheets

ULTRASONIC PROBE

This application is a continuation of application Ser. No. 07/203,526, filed on May 20, 1988, which in turn is a continuation of application Ser. No. 06/865,011, filed May 20, 1986, both prior applications being now abandoned.

BACKGROUND OF THE INVENTION

This invention relates to an ultrasonic probe used in an ultrasonic diagnostic apparatus for medical use.

It is a recent trend to use ultrasonic probes made of compound piezoelectric materials in the field of ultrasonic diagnostic apparatus for medical use and the like.

Such ultrasonic probe using compound piezoelectric materials has been conventionally known, including, for example, the construction mentioned in Proc. IEEE Ultrasonics Symposium, 1984, by A. A. Shaulov et al.

Referring now to FIGS. 1 and 2, the conventional array type ultrasonic probe using compound piezoelectric materials is described below.

FIG. 1 is a perspective view showing the essential parts, and FIG. 2 is a magnified sectional view of the portion of taking out lead wires thereof. Numeral 101 denotes a piezoelectric material, being composed of a piezoelectric ceramic 102 stretched in one-dimensional direction, and an organic polymer material 103 stretched in three-dimensional directions surrounding said piezoelectric ceramic 102. On one side of this compound piezoelectric material 101, a plurality of compounds 104 are disposed by vacuum evaporation by way of mask or the like, while a common electrode 105 is installed on the opposite side of the compound piezoelectric material 101 by vacuum evaporation, and an acoustic matching layer 106 made of epoxy resin or the like is adhered to the common electrode 105 side (the sound wave radiation side) in order to lead the sound waves efficiently to the subject to be examined. From the individual electrodes 104, lead wires 108 are taken out by wire bonding or similar means, and are connected to electric terminals (not shown).

Thus, by applying electrode signals controlled from outside into the electrodes 104, 105 at both sides of the compound piezoelectric material 101, ultrasonic waves can be radiated from the acoustic matching layer 106 side.

In this compound piezoelectric material 101, the piezoelectric ceramic 102 is made of PZT, and the organic high polymer material 103 may be made of epoxy resin or the like, and such compound piezoelectric material 101 can, in the electro-mechanical coupling coefficient, obtain a characteristic nearly equal to $k_{33}$ of the electro-mechanical coupling coefficient of the piezoelectric ceramic 102, and may be lowered in the acoustic impedance as compared with that of piezoelectric ceramic alone (in the case of PZT compound, it is about 20 to $35 \times 10^5$ g/cm$^2$·s). For example, if, by volume ratio, the piezoelectric ceramic 102 is used in an amount of 25%, and the organic polymer 103 of epoxy resin in an amount of 75%, the acoustic impedance is about $8 \times 10^5$ g/cm$^2$·s, and its matching with the subject such as the human body (of which acoustic impedance is 1.5 to $1.8 \times 10^5$ g/cm$^2$·s) is much better than in the case of piezoelectric ceramic alone, and only one layer of acoustic matching layer 106 is enough to improve the efficiency (sensitivity) of transmission and reception. Besides, since the piezoelectric ceramic 102 is one-dimensional direction only, leaks of sound waves to other elements (acoustic crosstalks) are few, which means that the orientation resolution is excellent.

Accordingly, the usefulness of ultrasonic probe using compound piezoelectric material 101 with a single acoustic matching layer 106 has been disclosed.

However, as in this conventional construction, when lead wires are taken out after forming an array of electrodes 104 by masking or other means on one side of the compound piezoelectric material 101, in spite of the advantage of high precision forming of electrodes 104 in an array form by employing the semiconductor manufacturing technology, it is practically rather difficult to take out lead wires 108 by wire bonding or other means after forming electrodes 104. That is, the compound piezoelectric material 101 is, as mentioned above, made of piezoelectric ceramic 102 and organic polymer 103 of epoxy resin, and this part is magnified in FIG. 2. More specifically, due to the difference in hardness and coefficient of thermal expansion between the piezoelectric ceramic 102 and organic polymer 103, the surface of the organic polymer 103 is not flat, but undulated, and it is hard to avoid this roughness. When electrodes 104 are formed on such undulated surface in a thickness of about 1 micron by vacuum evaporation or other means, the electrodes 104 are unevenly formed on the undulated surface of the compound piezoelectric material 101. It is extremely difficult to take out lead wires 108 by wire bonding uniformly and firmly on such non-flat surface. In particular, since wire bonding at the position of organic polymer 103 is difficult, it is required to take out lead wires 108 by wire bonding at the position of piezoelectric ceramic 102. However, at high frequency, the shape of the piezoelectric ceramic 102 becomes less than 70 microns, and wire bonding is barely possible. But when the lead wires 108 are taken out by wire bonding at the position of the electrodes 104 arranged in a plurality, the strength is lower and reliability is insufficient, or at higher frequency it is hard to take out lead wires 108.

As the mechanism of array type ultrasonic probe, meanwhile, the method of driving by sequentially scanning the transmission and reception signals to be applied to a plurality of array of electrodes 104, and the method of scanning by varing the running direction of the ultrasonic waves by driving, with a very slight time delay, the transmission and reception signal to be applied to a plurality of array of electrodes 104 are known. In these cases it is important that the sound waves may not propagate to the adjacent electrode parts when the arrayed electrodes 105 are driven, that is, the acoustic crosstalk be small, in the light of enhancing the orientation resolution. However, in such conventional structure, the acoustic matching layer 106 was not isolated from the plurality of electrodes 104, but was made of one continuous plate, and the unnecessary sound waves propagated to the adjacent electrode 104 parts from the acoustic matching layer 106 part, which caused deterioration of the orientation resolution.

SUMMARY OF THE INVENTION

This invention is intended to solve the above-discussed problems of the conventional technology, and it is hence a primary object of this invention to present an ultrasonic probe capable of picking up the electric terminals easily and enhancing the reliability.

It is another object of this invention to present an ultrasonic probe capable of enhancing the orientation resolution.

The ultrasonic probe of this invention has electrodes and electric terminals conducting to these electrodes, disposed on one principal plane of a compound piezoelectric material composed of piezoelectric ceramic and organic polymer, wherein these electrodes and electric terminals are divided into a plurality. On the other plane of the compound material, a common electrode is provided, and an acoustic matching layer is disposed on it either integrally or being divided corresponding to the divided electrodes.

BRIEF DESCRIPTION OF THE DRAWINGS

FIGS. 5 to 7 refer to other embodiments of this invention, in which FIG. 5 is a partial perspective view of the ultrasonic probe, FIG. 6 is a sectional view of FIG. 5, and FIG. 7 is a partial perspective view of the compound piezoelectric material.

DETAILED DESCRIPTION OF THE INVENTION

Figure 1:
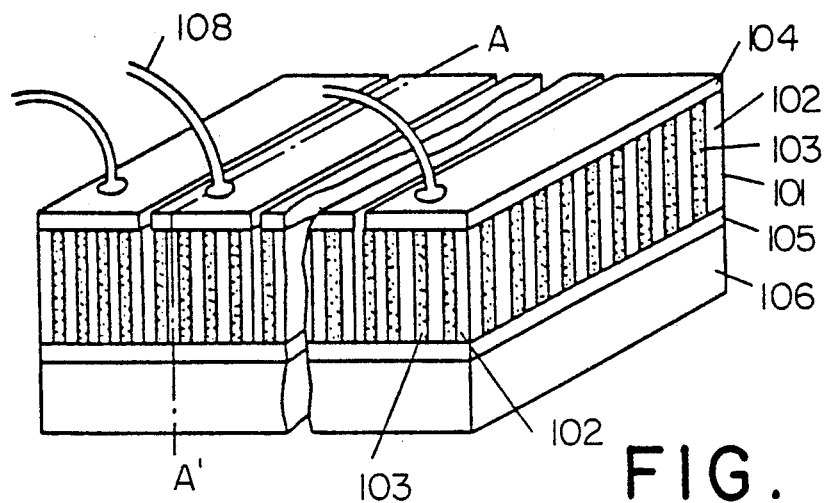
FIG. 1 is a perspective view showing a conventional ultrasonic probe made of compound piezoelectric material.
Figure 2:
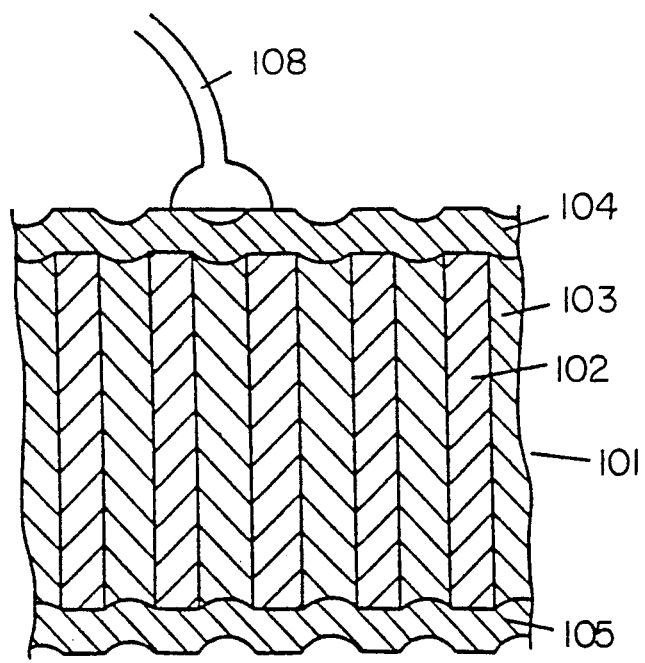
FIG. 2 is a sectional drawing of view A—A' of FIG. 1.
Figure 3:
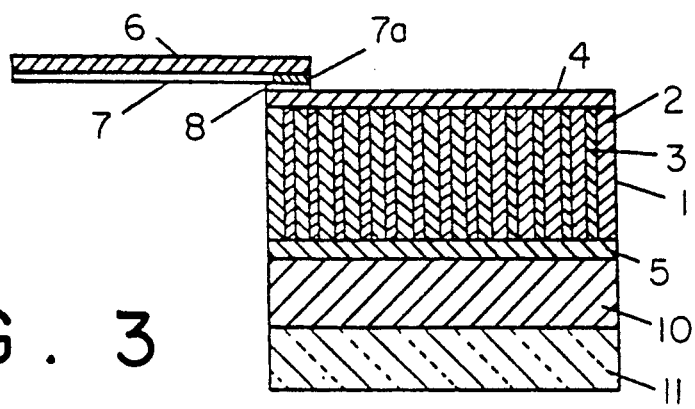
FIG. 3 is a cross sectional view of one of the embodiments of the ultrasonic probe according to this invention being made of compound piezoelectric material.
Figure 4:
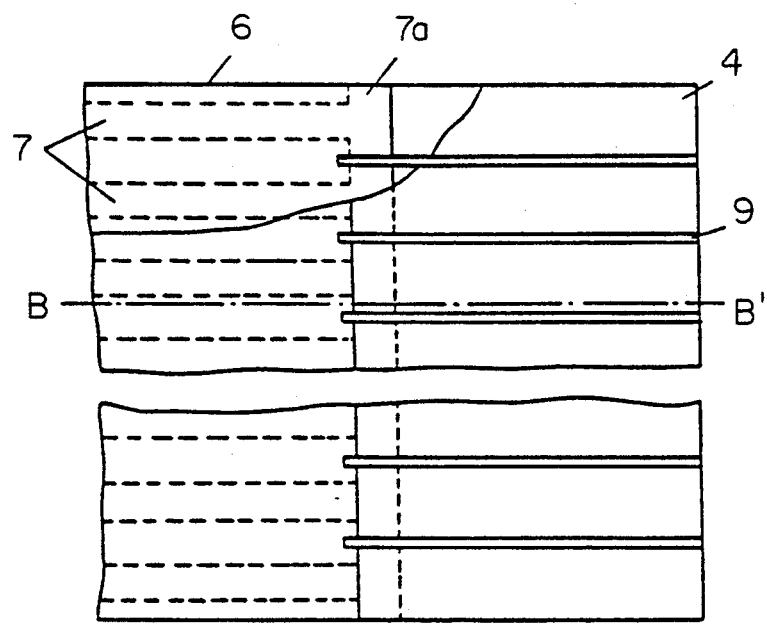
FIG. 4 is a plan view of the same ultrasonic probe as shown in FIG. 3.

One of the embodiments of this invention is described below while referring to the accompanying drawings. FIG. 3 is a sectional view of the ultrasonic probe of this invention, and FIG. 4 is a plan view of FIG. 3. As shown in FIG. 3 which is a sectional diagram of view B—B' in FIG. 4, a compound piezoelectric material 1 is composed of a piezoelectric ceramic 2 such as PZT, PCM or the like compound being stretched in one-dimensional direction, and a material small in acoustic impedance, such as epoxy resin or other organic polymer material 3, being stretched in three-dimensional directions in a manner to surround this piezoelectric ceramic. On both sides of the compound piezoelectric material 1, electrodes 4, 5 are disposed on the entire surface by vacuum deposition, plating or other means. A plus-side linkage part 7a of electric terminals 7 such as flexible cables formed in the same pattern as in the desired electrode intervals of a substrate 6 is adhered to the minus-side part of one of the electrodes 4 of the compound piezoelectric material 3 by solder or other conductor, and the electric terminals 7 and electrodes 4 of the compound piezoelectric material 1 are short-circuited. Then, at desired intervals as shown in FIG. 4, grooves are formed in the plus-side linkage part 7a of electric terminals 7 and the electrodes 4 of the compound piezoelectric material 1 by means of a dicing machine or the like to divide them. Next, as shown in FIG. 3, an acoustic matching layer 10 made of epoxy resin or the like is formed, by pouring in or other means, on the electrode (common electrode) 5, opposite to the electrodes 4 to which the electric terminals 7 are connected, and an acoustic lens 11 such as silicone rubber is formed on this acoustic matching layer 10 in order to focus the ultrasonic waves as required.

In this way, electrodes 4 are disposed on the whole surface of the compound piezoelectric material 1, and electric terminals 7 are adhered to part of the electrodes 4 by using conductive adhesive 8 or the like to short-circuit, then the electrodes 4 of the compound piezoelectric material 1 and the linkage part 7a of the electric terminals 7 are divided in an array form. Therefore, masking conventionally required to arrange the electrodes in an array form is not needed, and the frequency becomes higher and the shape of the piezoelectric ceramic 2 is smaller, so that the terminals 7 can be taken out easily, without any problem, if the electrode intervals of array are narrow. Moreover, the electric terminals 7 are formed on the substrate 6 and are high in strength, and they are directly adhered to the electrodes 4, without being coupled with lead wires, to short-circuit, so that the take-out parts of the electric terminals 7 are very strong, which contributes to reliability. In this embodiment, incidentally, first the electrodes 4 are disposed on the compound piezoelectric material 1, and then electric terminals 7 are adhered by means of conductive adhesive 8 or the like to conduct with each other, but in this invention it is also possible to adhere the electric terminals to part of the compound piezoelectric material 1 by using an insulating material such as epoxy resin, before installing electrodes 4 on the compound piezoelectric material 1, and then vacuum evaporate the electrodes 4 to part of the electric terminals 7 and compound piezoelectric material 1 to conduct, and form by dividing the electrodes 4 in an array form. Besides, this embodiment refers to the application to the so-called array type ultrasonic probe arranged in a linear form, but it is evident that this invention may be also applied to various types of ultrasonic probe, such as two-dimensional layout ultrasonic probe and arc layout ultrasonic probe.

According to this invention, as clear from the description above, electrodes and electric terminals to conduct to these electrodes are provided on the principal plane of a compound piezoelectric material, and these electrodes and electric terminals are divided into plurality to take out electric terminals. Therefore, as the frequency becomes higher, the size of the piezoelectric ceramic of the compound piezoelectric material becomes smaller, and if the electrode intervals in the array become narrow, the electric terminals can be picked up easily, and the short-circuiting parts of the electrodes and electric terminals are increased in strength, so that the reliability may be improved.

Figure 5:
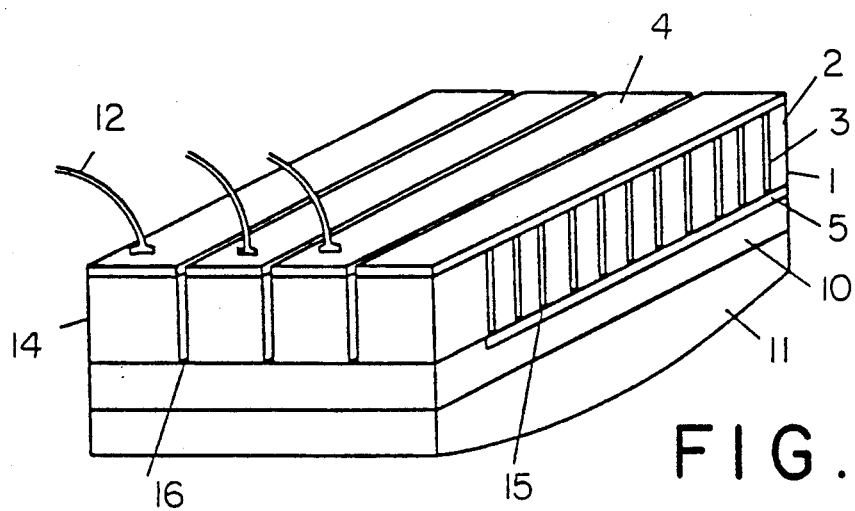
Figure 6:
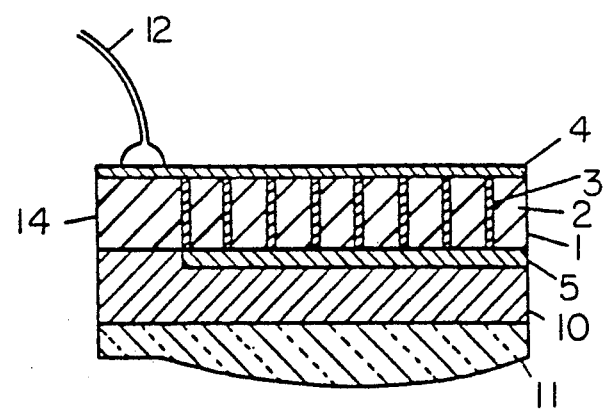
Figure 7:
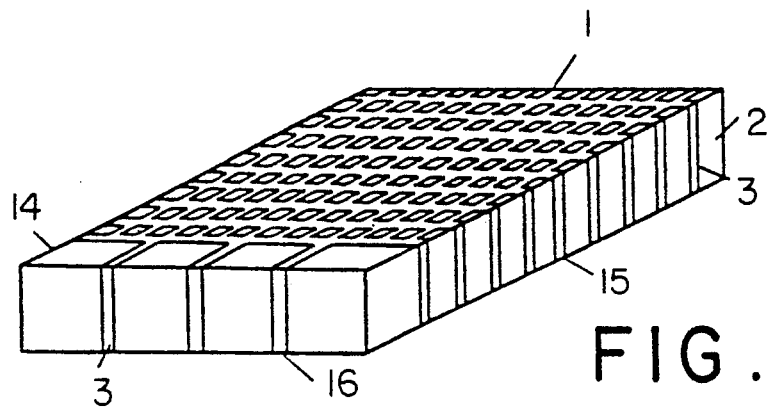

FIG. 5 is a partial perspective view of the ultrasonic probe in another embodiment of this invention, FIG. 6 is its sectional view, and FIG. 7 is a partial perspective view of the compound piezoelectric material.

As shown in FIG. 5, the compound piezoelectric material 1 is composed of a piezoelectric ceramic 2 of PZT, PCM or the like compound stretched in one-dimensional direction, and organic polymer material 3 such as epoxy resin stretched in two-dimensional directions being adjacent to said piezoelectric ceramic. The piezoelectric ceramic 2 is divided by forming dividing grooves 15 in grating form by dicing machine or the like, leaving only the electric terminal take-out portion 14, and this portion 14 is also divided by dividing grooves 16 so as to be at same intervals as in the array-shaped electrodes 4 mentioned later. These dividing trenches 15, 16 are filled up with organic polymer material 3 and are hardened. At this time, the organic polymer material 3 should be preferably deformed in vacuum in order to fill up uniformly with few bubbles. These piezoelectric ceramic 2 and organic polymer material 3 are machined to a thickness of desired frequency by polishing or other means, and make up the compound piezoelectric material 1. Therefore, since the electric terminal take-out portion 14 is almost completely made of piezoelectric ceramic, it does not function as compound piezoelectric material. As shown in FIGS. 5 and 6, on one side of the compound piexoelectric material 1, a plurality of array-formed electrodes 4 are provided by vacuum evaporation or similar method by way of mask or the like at the intervals of dividing grooves 16, and on the other side, a common electrode 5 is provided, by vacuum evaporation or other method, excluding the electric terminal take-out portion 14. On the outside of the common electrode 5, an acoustic matching layer 10 made of epoxy resin or the like in the thickness of $\frac{1}{4}$ wavelength is provided by adhering or pouring. Furthermore, as required, an acoustic lens 11 of silicone rubber or the like is provided by adhering or pouring in order to focus ultrasonic waves on the outside of the acoustic matching layer 10. At the electrodes 4 arranged in a plurality of arrays, the electric terminals 12 are taken out by wire bonding or other means from the positions corresponding to the electric terminal take-out portion 14.

Thus, since the electric terminal take-out portion 14 is made of piezoelectric ceramic 2 almost completely when fabricating the compound piezoelectric material 1, the electric terminals 12 can be taken out easily and firmly by wire bonding or other method. Therefore, the take-out reliability is high. In addition, since common electrode 5 is not provided at the position corresponding to the electric terminal take-out portion 14 on the opposite side of the array-formed electrodes 4 in the compound piezoelectric material 1, this portion does not vibrate. That is, since only the compound piezoelectric material 1 other than the electric terminal take-out portion 14 vibrates, a desired ultrasonic beam may be obtained. Furthermore, since the electric terminal take-out portion 14 of the piezoelectric ceramic 2 is divided at the same intervals as the plural arrays of electrodes 4, acoustic crosstalk to the adjacent elements may be reduced, so that an ultrasonic resolution high in orientation resolution may be obtained.

In the above embodiment, incidentally, first the electric terminal take-out portion 14 of the piezoelectric ceramic 2 was divided at the same intervals as the arrays of electrodes 4, and then arrays of electrodes 4 were evaporated by using mask or the like, but other methods may be applicable. For example, electrodes for forming an array of electrodes 4 are provided on the whole surface on one side of the compound piezoelectric material 1 having electric terminal take-out portion 14, and a common electrode 5 is provided on the other side, then an acoustic matching layer 10 is disposed on this common electrode 5, and the electrodes and compound piezoelectric material 1 are divided into arrays by dicing machine or the like to compose arrays of electrodes 7, and finally the electric terminals 12 are taken out by wire bonding or other method. Or, similar to the case shown in FIGS. 3 and 4, it may be also possible to provide electrodes for making up arrays of electrodes 4 on the whole surface on one side of the compound piezoelectric material 1 having electric terminal take-out portion 14, dispose a common electrode 5 on the other side, install an acoustic matching layer 10 on this common electrode 5, provide plate-shaped terminals as plate-shaped electric terminals 11, by soldering or by using conductive adhesive, on the electrodes at the position corresponding to the electric terminal take-out portion 14 of the compound piezoelectric material 1, and divide the electric terminals, electrodes, and compound piezoelectric material 1 into arrays, thereby taking out the electric terminals 11.

These embodiments also refer to applications into the so-called array type ultrasonic probe arranged in a linear form, but it is evident that this invention may be equally applied to other types of ultrasonic probe, such as two-dimensional layout ultrasonic probe and arc layout ultrasonic probe.

Thus, in this embodiment, the electric terminal take-out portion is provided in the piezoelectric ceramic of the compound piezoelectric material, and arrays of electrodes are provided on one side of this compound piezoelectric material, while a common electrode is provided on the other side, and the electric terminals are taken out from the arrays of the electrodes at the position corresponding to the electric terminal take-out portion. Therefore, as the frequency is higher, if the size of the piezoelectric ceramic of the compound piezoelectric material is reduced or the intervals of arrays of electrodes are narrowed, the electric terminals can be taken out easily. Moreover, since the electric terminal take-out portion is high in strength, the reliability may be enhanced.

Figure 8:
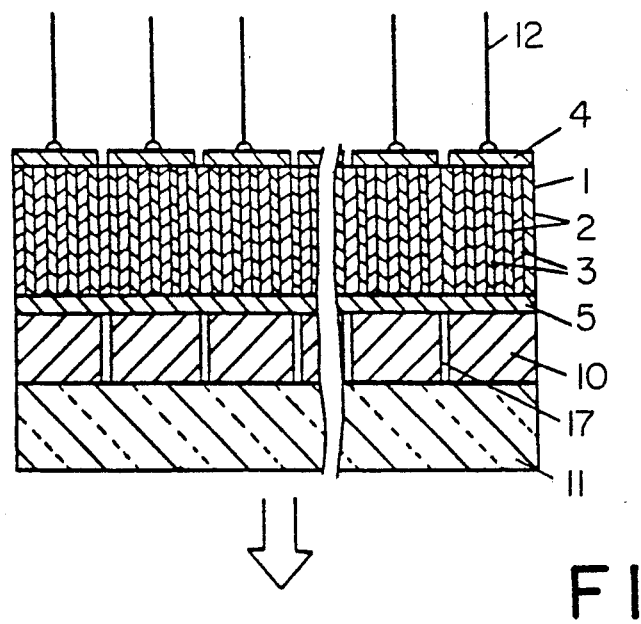
FIG. 8 depicts a further different embodiment of the ultrasonic probe of this invention.

FIG. 8 is a sectional view of an ultrasonic probe in a further different embodiment of this invention, in which the compound piezoelectric material 1 is made of a piezoelectric ceramic 2 of PZT, PCM or the like compound stretched in one-dimensional direction, and an organic polymer 3 such as epoxy resin stretched in three-dimensional directions being adjacent to this piezoelectric ceramic 2. If, for example, the PZT compound piezoelectric ceramic 2 and organic polymer 3 made of epoxy resin are used in amounts of 25% and 75% by volume, the acoustic impedance is $8 \times 10^5$ g/cm$^2$·s. On one side of this compound piezoelectric material 1, a plurality of electrodes 4 are arranged at specified intervals, while a common electrode 5 is formed on the other side by vacuum deposition or other process. On this common electrode 5, an acoustic matching layer 10 in a thickness of $\frac{1}{4}$ of wavelength is formed by adhering or pouring. Supposing the subject is a human body (of which acoustic impedance is 1.5 to $1.8 \times 10^5$ g/cm$^2$·s), the suited acoustic impedance of the acoustic matching layer 10 is about 3 to $4 \times 10^5$ g/cm$^2$·s, and the material having this value is epoxy resin, and epoxy resin is used in the acoustic matching layer 10. This acoustic matching layer 10 is divided by forming dividing grooves 17 by dicing machine or the like at the same intervals as the above electrodes 4. On this divided acoustic matching layer 10, an acoustic lens 11 of silicone rubber or similar material is formed by adhering or pouring in order to focus ultrasonic waves, and the dividing grooves 17 of each acoustic matching layer 10 are filled up with adhesive or same material as acoustic lens 11. As the material to fill up the dividing grooves 17 of the acoustic matching layer 10, any substance which has a great difference in acoustic impedance from the acoustic matching layer 10 and has a great ultrasonic damping factor may be used, such as a blend of silicone rubber and micro-balloons.

Thus, by dividing the acoustic matching layer 10 at the same intervals as the electrodes 4 arranged in a plurality on the compound piezoelectric material 1, propagation of sound waves to adjacent electrodes 4 can be prevented, and it is evident that the acoustic crosstalk can be notably decreased. Therefore, an ultrasonic wave picture high in orientation resolution may be obtained.

In this embodiment, first the acoustic matching layer 10 was formed on the compound piezoelectric material 1 by adhering or pouring, and was divided, but it is also possible to form by preliminarily forming the acoustic matching layer 10 on the compound piezoelectric material 1 by adhering or pouring, dividing the acoustic matching layer 10, leaving about 1/10 of the thickness or completely, at the same intervals as the electrodes 4 arranged in a plurality on the compound piezoelectric material 1, filling the divided grooves 17 with silicone rubber or similar material, and adhering on the common electrode plane 5 of the compound piezoelectric material 1.

By this embodiment, the acoustic matching layer provided at the sound wave transmission and reception side of the compound piezoelectric material which transmits and receives ultrasonic waves is divided at the same intervals as the electrodes disposed in a plurality at specified intervals on the side opposite to the sound wave transmission and reception side of the compound piezoelectric material. Therefore, acoustic crosstalk to the adjoining electrode parts can be sizably decreased, and an ultrasonic probe possessing a high orientation resolution performance may be obtained.

What is claimed is:

1. An ultrasonic probe comprising a compound piezoelectric material made of piezoelectric ceramic and an organic polymer material, a ceramic material as an electric terminal takeout portion along the end portion of said compound piezoelectric material, plural-line array electrodes provided on one surface of said compound piezoelectric material and said ceramic material, said ceramic material being divided at the same interval as that of the array electrodes, the same material as said organic polymer material being provided in the grooves which divide said ceramic material, end electric terminals being provided which are taken out form the array electrode portion of said ceramic material corresponding to the electric terminal takeout portion from the array electrodes provided on said complex piezoelectric material.

2. The ultrasonic probe of claim 1, wherein the piezoelectric ceramic in the electric terminal take-out portion is divided by grooves at same intervals as the array-formed electrodes, and the dividing grooves are filled with organic polymer material.

3. The ultrasonic probe of claim 1, wherein the common electrode is provided on the compound piezoelectric material, excluding the area for the electric terminal take-out portion.

4. The ultrasonic probe of claim 1, wherein the piezoelectric ceramic is two component (PZT) or three component (PCM) piezoelectric materials stretched in one-dimensional direction, and the organic polymer is an epoxy resin stretched in three-dimensional directions, and both are used at the ratio of 1:3 by volume.

* * * * *